United States Patent [19]

Lutz et al.

[11] 4,404,406

[45] Sep. 13, 1983

[54] OXIDATION OF ISOBUTANE UNDER SUPER-CRITICAL CONDITIONS

[75] Inventors: Eugene F. Lutz; Elton G. Foster, both of Houston, Tex.

[73] Assignee: Shell Oil Company, Houston, Tex.

[21] Appl. No.: 308,631

[22] Filed: Oct. 5, 1981

[51] Int. Cl.³ .................................................. C07C 179/02
[52] U.S. Cl. ..................................... 568/571; 568/565
[58] Field of Search ................................. 568/571, 565

[56] References Cited

U.S. PATENT DOCUMENTS

| | | | |
|---|---|---|---|
| 2,845,461 | 7/1958 | Winkler et al. | 568/571 |
| 3,478,108 | 11/1969 | Grane | 568/571 |
| 3,502,740 | 3/1970 | Zajacek et al. | 568/571 |
| 3,816,540 | 6/1974 | Barone | 568/571 |
| 3,855,314 | 12/1974 | Dubois | 568/571 |
| 3,907,902 | 9/1975 | Grane | 568/571 |
| 3,974,228 | 8/1976 | Barone | 568/571 |
| 4,128,587 | 5/1978 | Jubin | 568/571 |

FOREIGN PATENT DOCUMENTS 7709269  5/1978  Netherlands .................. 568/571

OTHER PUBLICATIONS

Winkler, "Industrial and Eng. Chem.", vol. 53, (1961), p. 655.

Primary Examiner—Werren B. Lone
Attorney, Agent, or Firm—Richard F. Lemuth

[57] ABSTRACT

In the preparation of tertiary-butyl hydroperoxide by the direct oxidation of isobutane, the production of tertiary-butyl hydroperoxide, expressed as the quantity of the compound prepared per unit of reactor volume per unit of time, is enhanced by conducting the oxidation in a dense, supercritical phase reaction mixture at a temperature in excess of the critical temperature of the mixture, at a pressure in excess of the critical pressure of the mixture, and under conditions relating to composition of the mixture.

16 Claims, 1 Drawing Figure

OXIDATION OF ISOBUTANE UNDER SUPER-CRITICAL CONDITIONS

BACKGROUND OF THE INVENTION

This invention relates to an improved process for the production of tertiary-butyl hydroperoxide by direct oxidation of isobutane.

Tertiary-butyl hydroperoxide (hereinafter sometimes referred to as TBHP) is a material of commerce having application as a catalyst, as an initiator for free radical-type reactions and as a starting material or intermediate in the production of valuable chemicals such as oxirane compounds and other organic hydroperoxides.

Because of the ready availability and low cost of starting materials, significant effort has been focused in the past specifically on the preparation of TBHP by direct oxidation of isobutane. Previous disclosures in this area of technology have recognized that the reaction between isobutane and molecular oxygen is inherently nonselective in that significant amounts of tertiary-butyl alcohol and minor amounts of other oxygenated compounds such as acids, aldehydes, ketones and other alcohols are formed in addition to the desired TBHP. According to the work of Winkler et al. (U.S. Pat. No. 2,845,461 and also "Liquid Phase Oxidation of Isobutane," Industrial and Engineering Chemistry, vol. 53 (Aug. 1961), page 655) the formation of by-products other than the desired TBHP is promoted by the presence of substantial amounts of isobutane in the vapor phase during the course of the oxidation reaction. The oxidation of isobutane had therefore been conducted in the vapor phase in the presence of a catalyst, particularly hydrogen bromide, at lower reaction rate to produce a mixture containing unacceptably large quantities of by-products, and contaminated with catalyst derivatives, e.g., organic bromides. It is taught by Winkler et al that a reaction product consisting essentially of TBHP and tertiary-butyl alcohol can be obtained in high yield by reacting isobutane with molecular oxygen in the liquid phase of a two phase (i.e., vapor and liquid) mixture at a temperature of from about 100° to 150° and a pressure of at least 400 psig (up to 700 psig) provided the reaction is carried out in a reaction medium in which the presence of any substantial amount of metal ions is excluded and wherein at least a substantial part of the isobutane is in the liquid phase. Liquid-phase isobutane oxidation in the presence of a polyphosphate catalyst is taught by Barone et al. (U.S. Pat. No. 3,816,540). Oxidation of isobutane in the liquid phase, generally according to the teachings of Winkler et al, is believed to be a current standard for practice in the art.

In spite of its commercial acceptance, the oxidation of isobutane in the liquid phase remains an inefficient method for preparation of TBHP. For instance, the reaction is one of low rate, generally requiring a reaction time of several hours. Furthermore, it is recognized that under any given reaction conditions there inherently exists an inverse relationship between isobutane conversion and TBHP selectivity, so that an increase in one is associated with a decrease in the other.

The art contains a number of disclosures of methods for improving some aspect of the overall liquid phase oxidation process. Winkler et al. teach that the oxidation reaction rate in the liquid phase can be enhanced by carrying out the oxidation above the critical temperature of isobutane (134° C.). However, for practice at such elevated temperatures it is necessary according to such teachings that the reaction be conducted in a liquid medium based upon a relatively high boiling point solvent. At temperatures above the critical temperature of isobutane, but below the critical temperature of the reaction mixture, a liquid-phase oxidation can be then accomplished. The use of externally-supplied reaction solvents, e.g., organic acids, is discouraged by Winkler et al as tending to increase the complexity of the oxidation reaction and subsequent product separation and recovery. Winkler et al instead propose oxidation above 134° C. in a liquid phase (of a vapor-liquid mixture) in which the reaction products, principally tertiary-butyl alcohol and TBHP, act as solvent. However, in comparison with lower temperature liquid-phase oxidation, such practice is said to adversely influence the yield of TBHP. Moreover, it is taught that reaction in the liquid phase, at a temperature above 134° C., and without an external supply of solvent, requires that the liquid reaction phase have a composition corresponding to a conversion of isobutane of at least 20% and preferably of more than 30%. Because of the recognized inverse relationship between isobutane conversion and selectivity to TBHP, isobutane oxidation at a temperature above 134° C. according to these teachings is a process in which selectivity to TBHP is inherently limited. Furthermore, any enhanced rate realized in such a process is in large degree the result of the high conversions achieved—since TBHP is itself an initiator for isobutane oxidation, the rate of conversion increases as the concentration of TBHP in the reaction mixture increases. On the whole, the liquid phase oxidation reaction of Winkler et al., even above the 134° C. critical temperature of isobutane, remains a process characterized by a relatively slow rate of reaction and a low selectivity for TBHP.

The relevant art also provides disclosure of more recent work relating to improving the conversion or selectivity of non-catalytic liquid-phase isobutane oxidation. For instance, U.S. Pat. No. 3,478,108 to Grane describes the effects of the addition of minor amounts of water (up to 6 percent) upon the conversion and selectivity in the liquid phase oxidation of isobutane with molecular oxygen to afford TBHP and tertiary-butyl alcohol in accordance with the reaction conditions generally described by Winkler et al. Further U.S. Pat. No. 3,907,902 to Grane discloses that the selectivity with which isobutane is converted to TBHP in the direct oxidation reaction can be enhanced by the addition of small amounts of certain alcohols (isopropyl alcohol) to the oxidation reaction zone wherein molecular oxygen is reacted with isobutane, again according to the general conditions described by Winkler et al. Practice according to such methods, however, may prove undesirable, for like the use of externally-supplied reaction solvents disclosed by Winkler et al. addition of foreign substances to the reaction mixture may have adverse effect upon the complexity of the reaction and the subsequent product recovery.

Furthermore, the greatest benefits of these processes, with respect to enhanced selectivity, for instance, are realized at a reaction temperature of about 134° C. and less.

With regard to all such isobutane oxidation processes of the prior art, while a given process improvement may enhance the reaction rate or the ultimate percent conversion of isobutane or the selectivity to TBHP, it is not apparent that any such alternative affords any substantial overall increase in the productivity of isobutane oxidation for TBHP preparation, in comparison to the basic liquid phase reaction process of Winkler et al. As the term is used herein, productivity is defined as the multiplication product of the rate of isobutane conversion during the oxidation reaction and the selectivity of the reaction for TBHP, and expresses the quantity of TBHP produced per unit volume of reaction mixture per unit of reaction time. For realization of objects that are well known in the art, and for accomplishment of other objects which will be described herein, a process for the direct, noncatalytic oxidation of isobutane which provides for such an improvement would be most desirable.

SUMMARY OF THE INVENTION

An improved process has now been discovered for TBHP production which comprises isobutane oxidation in a supercritical phase reaction mixture. In other words, TBHP preparation via isobutane oxidation is conducted, at least in part, at a temperature above the critical temperature of the reaction mixture and at a pressure above the critical pressure of the mixture. As will be hereinafter more thoroughly described, in order to attain the desired improvement, restrictions are also necessarily placed upon the composition of the oxidation reaction mixture, particularly with respect to minimum isobutane reactant content and maximum oxygen reactant content. Under specified process conditions, enhanced production of TBHP in terms of quantity of TBHP per unit volume of reaction mixture per unit of time is achieved without adverse effect on other aspects of the isobutane oxidation, for instance, without sacrifice in reaction selectivity for TBHP. In a preferred aspect of the invention which provides optimum process results, limitation is further made with respect to the content of product TBHP in the reaction mixture, or, somewhat equivalently, with respect to maximum isobutane conversion.

In terms of enhancing the quantity of TBHP prepared per unit volume of reaction mixture volume per unit of reaction time, the invention provides substantial improvement over the performance of the conventional oxidation reaction conducted in the liquid phase of a vapor-liquid mixture. This improvement is of substantial importance for the particular oxidation reaction here of interest in view of a combination of factors which are known to govern reaction performance. From conventional practice it is recognized that the oxidation of isobutane to TBHP is characterized by slow reaction rate, requiring correspondingly large reactor vessels. At the same time the reaction is known as one which proceeds best only at relatively high pressures, e.g., 400 psig or greater. Still further, since the presence of even very small quantities of metal ions in the reaction mixture has substantial adverse effect upon process results, special provisions must be made with regard to the materials of construction of the reactor and passivation treatment of reactor surfaces. While considerations of economy and operating convenience generally provide incentive for productivity improvement in any reaction process, these factors specific to isobutane oxidation render the process of the present invention all the more valuable in the instance of TBHP preparation.

Practical advantages may be taken of the improvement provided by the invention in any one or more of a number of ways. For instance, the relatively high reaction selectivities to TBHP heretofore attainably only at a low rate of isobutane oxidation are now achieved at a substantially increased rate, permitting the use of small reaction volumes and/or shorter reaction times. In a complementary aspect, at reaction rates comparable to those of conventional liquid-phase oxidation processes, the invention provides a selectivity to TBHP of a magnitude not heretofore realized. Enhanced productivity can be accomplished under operation of the invention without the presence of externally-supplied reaction solvents and additives, as are known to the art.

DESCRIPTION OF THE PREFERRED EMBODIMENTS

The isobutane subject to direct oxidation in accordance with the invention is suitably of a quality comparable to that conventionally employed for purposes of TBHP preparation. Preferably the isobutane reactant is substantially pure, that is, substantially free of other hydrocarbons and metal ion contaminants. Similarly, the molecular oxygen employed as a reactant in the process of the invention very suitably meets typical specifications heretofore imposed on oxygen reactants for hydroperoxide manufacture. For example, the oxygen reactant may be essentially pure oxygen or molecular oxygen in admixture with an inert fixed gas, e.g., oxygen diluted with nitrogen. For reasons which will be described hereinbelow, a clear preference may be stated for a molecular oxygen reactant which is substantially pure oxygen, for instance, as is obtainable from any one of a variety of commercial sources.

While it is commonly known in the art that the hydroperoxides of a large variety of organic compounds having a tertiary carbon atom can be prepared by reaction with molecular oxygen, it is believed that the process of the present invention is uniquely suited only to the oxidation of isobutane. Other compounds generally suitable for reaction with oxygen to yield hydroperoxides have critical temperatures substantially greater than that of isobutane. Oxidation of these other compounds in a manner like that of the invention but in excess of such higher critical temperatures would result in significant decomposition of the product hydroperoxide and excessive by-product formation.

For purposes of this invention, the isobutane and molecular oxygen reactants are contacted in a reaction mixture under specified conditions of temperature, pressure and reaction mixture composition. Either initially or during the course of the reaction, the mixture will comprise, in addition to isobutane and oxygen, the desired product TBHP, significant quantities of the principal reaction by-product tertiary-butyl alcohol, and lesser quantities of other oxygenated by-product compounds (acids, aldehydes, ketones, and other alcohols) commonly associated with isobutane oxidation. Most preferably, the reaction mixture is essentially free of other substances. However, the mixture may suitably contain small quantities of other reaction initiators, additives, solvents, promoters, or catalysts as are reported in the art to be of benefit in the reaction of interest. With regard to the presence of such substances in the mixture, care must be taken to maintain the reactant/product mixture in the supercritical phase.

It is an essential aspect of the present invention that isobutane oxidation be carried out at least in part at a temperature greater than the critical temperature of the reaction mixture. With respect to operation in the supercritical phase, what is of primary importance is conducting the reaction, at least in part, at a temperature in excess of the critical temperature of the mixture, insofar as this mixture contains reactants and products indigenous to the oxidation reaction. Preference is given to operation at temperatures greater than about 140° C., while temperatures in the reaction mixture above about 170° C. are preferably avoided because of their adverse influence upon the selectivity of the reaction to the desired TBHP product. A more preferred range of process temperature extends from about 145° to 165° C., with the range of about 150° to 160° C. being most preferred.

Isobutane oxidation in accordance with the invention is necessarily conducted at a pressure in excess of the critical pressure of the reaction mixture. Again, it is the critical pressure of the reaction mixture insofar as it contains reactants and products indigenous to the oxidation reaction that is of particular interest for purposes of the invention. Advantage with respect to TBHP production is observed as processing pressure is further increased in the supercritical region, although the magnitude of the incremental improvement in TBHP production per unit of pressure increase generally lessens as process pressure is raised. Thus, as an example, for operation of the invention at a temperature of 155° C., there is substantial advantage associated with increasing process pressure from about 750 to 930 psig, and much less advantage in further increasing pressure from 930 to 1100 psig, all of these pressures being above the critical pressure of the reaction mixture. Pressure was not reported to have any significant influence upon the results of isobutane oxidation in prior art liquid-phase reactions, so long as it was sufficient to maintain the reaction in the liquid state. For purposes of the invention, a pressure of at least 700 psig is preferred, a pressure of at least 800 psig is more preferred. While no adverse effects on process performance are known to accompany operation of the present invention at very high pressure, e.g., 2000 or 3000 psig, for reasons relating to design, construction, and operation of reactors and auxiliary processing equipment, it is preferred that the invention be practiced at a pressure of less than about 1800 psig. Practice in the range of about 900 to 1500 psig is considered most preferred.

Figure 1:
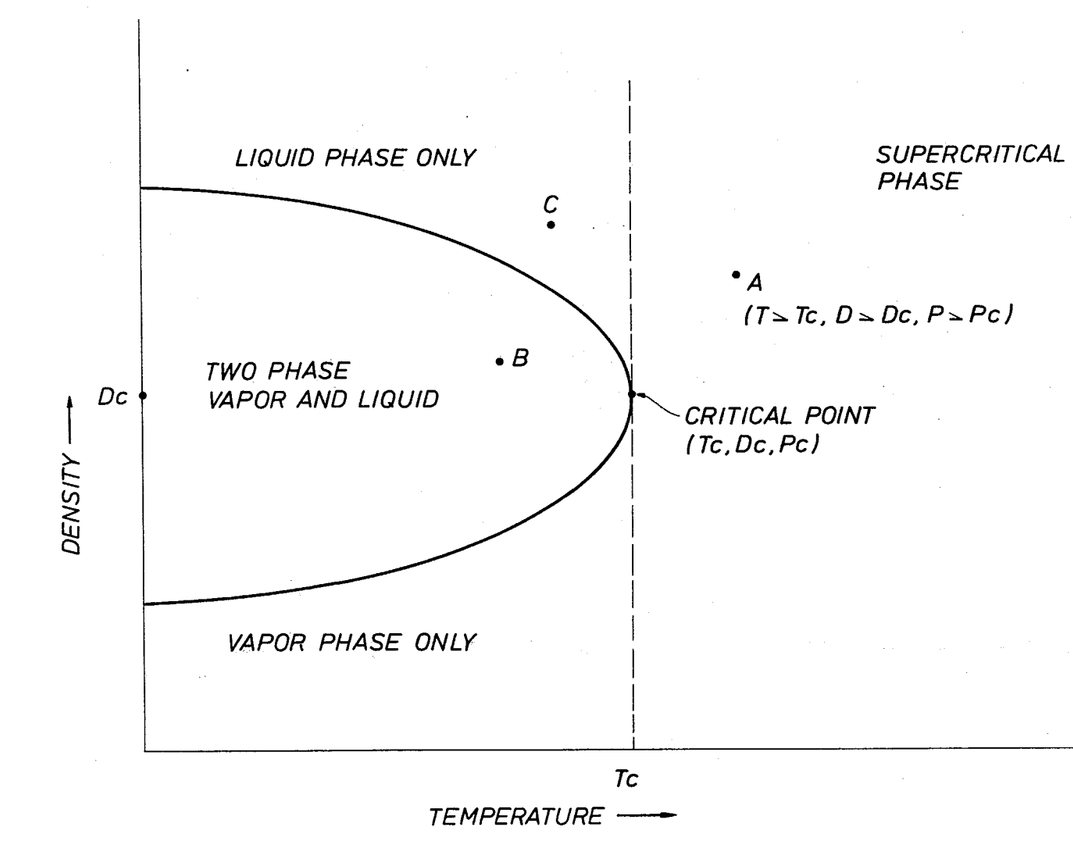

The reaction mixture is herein described as a supercritical phase, using this terminology in the conventional sense. By definition, there is an absence in such a mixture of an identifiable liquid phase (e.g., of a two-phase vapor liquid mixture) comprising any substantial quantity of isobutane, as is necessary for practice in accordance with the teachings of Winkler and others. Particular illustration of reaction parameters characterizing the supercritical phase, and of distinction between these parameters and conditions associated with conventional oxidation in the liquid phase, is provided by reference to the attached drawing. The drawing depicts in generalized form a plot of the phase behavior of a substance (e.g., an isobutane oxidation mixture), as a function of density and temperature, in the vicinity of the critical point. The critical point corresponds to the critical temperature (Tc), critical density (Dc) and also critical pressure (Pc) of the mixture. (It will be appreciated that specification of any two of these three variables is sufficient to characterize the phase behavior of a given mixture. The plot of the drawing is made on the basis of density instead of pressure to simplify the illustration.) As shown, at temperatures less than the critical temperature Tc, the mixture may have one of three forms, depending upon its density (or pressure). At lower density (lower pressure), the mixture is in the vapor state; at moderate density (moderate pressure), the mixture exists as two phases (vapor and liquid) in equilibrium; at higher density (higher pressure) the mixture exists as a single liquid phase. As the critical temperature and pressure are approached, the properties of the liquid and vapor phases in a two phase mixture approach each other, and at the critical temperature and pressure, the properties of the two phases become identical, and the phase boundary disappears. In the supercritical region above the critical temperature, gas and liquid can no longer exist as separate phases, and there is but a single supercritical phase. The properties of this supercritical phase, particularly the density, depend strongly upon the temperature and pressure. As the pressure increases, the density increases. As will be discussed below, this invention is particularly concerned with reaction in the supercritical region where the pressure is sufficiently high to give an isobutane partial density of at least 12 lb/cu. ft.

The critical temperature is also referred to in the art as the temperature above which it is impossible to liquefy a substance no matter how great a pressure is applied.

With particular reference to the attached drawing, practice in accordance with the invention is exemplified by operation at the point designated A on the drawing, that is, in the supercritical phase at a temperature above the critical temperature (and also at a pressure above the critical pressure of the reaction mixture). Practice in accordance with the prior art is exemplified by operation at the point designated B, that is, in the two phase (vapor and liquid) region below the critical temperature of the mixture.

It should be emphasized that the temperature designated Tc in the drawing is the critical temperature of the isobutane oxidation reaction mixture and not the critical temperature of isobutane itself. The reaction mixture contains, in addition to isobutane, the oxygen reactant and the oxidation reaction products. As the reaction proceeds in the mixture, there is an increase in the content of the mixture with respect to reaction products and a corresponding increase in the critical temperature of the mixture. The prior art indicates that the desired reaction may take place above the critical temperature of isobutane. However, at the same time, this art requires that in such a case the mixture necessarily contains a sufficient quantity of a solvent so that the reaction temperature remains below the critical temperature of the mixture and the mixture has distinct liquid and vapor phases. On the other hand, during processing under the invention the reaction temperature is above the critical temperature of isobutane and also above the critical temperature of the reaction mixture.

It will be apparent, from the fact that changes in the composition and critical conditions of the reaction mixture occur as isobutane oxidation proceeds, that a reaction temperature which is greater than the critical temperature of the mixture at a relatively low level of isobutane conversion may be less than the critical temperature of the mixture at higher levels of isobutane conversion. The invention suitably comprises practices under which the oxidation reaction is conducted in part in a first process stage in the supercritical phase at a temperature above the critical temperature of the reaction mixture and at a pressure above the critical pressure of the mixture, and thereafter continued in a second stage at a temperature and/or pressure below the critical conditions. For instance, if a semi-batch isobutane oxidation reaction in accordance with the invention is conducted at a constant temperature of about 155° C., this reaction temperature will typically exceed the critical temperature of the reaction mixture until isobutane conversion reaches a level of about 10%; thereafter, the oxidation can be continued at a reaction temperature below the critical temperature of the reaction mixture. Likewise, it is possible, although not recommended, to operate under the invention by carrying out only part of the overall oxidation under the specified conditions of isobutane partial density, and oxygen concentrations. In such cases, however, precaution recognized in the art must be taken to avoid operation under hazardous conditions.

Contact between oxygen and isobutane in the supercritical dense phase mixture may be brought about in a reaction zone comprising one or more reactors of conventional design. Because the TBHP-containing mixture is unstable if it contains any substantial amount of metal ions, it is known that reactor surfaces in contact with the mixture must not be formed of materials which release such ions. Reactors having a surface of glass, ceramic, porcelain, or like non-porous, smooth-surfaced, non-catalytic materials are known to be particularly suitable. Reactors having metal surfaces in contact with the reaction mixture are known to be suitable in certain circumstances. For instance, reactors with stainless steel surfaces may be employed, although the surfaces are first preferably passivated by treatment according to conventional methods, for instance, by treatment with nitric acid and sodium pyrophosphate, to eliminate therefrom metal particles or ions capable of being transferred into the oxidation reaction mixture. Because of the recognized influence of reactor surfaces, it is often desirable that reactors be utilized which are characterized by a relatively small ratio between the surface area exposed to reaction mixture and the volume of the mixture.

In order to obtain improvement in isobutane oxidation for TBHP production in accordance with the object of the invention, it is necessary that the supercritical oxidation reaction mixture contain isobutane in substantial concentration. Expression is herein given to the content of isobutane reactant in the mixture in terms of the partial density of isobutane, i.e., as the weight of isobutane reactant per unit volume of reaction mixture or, equivalently, as the total density of the mixture multiplied by the weight fraction of isobutane therein. For purposes of the invention, isobutane partial density is necessarily greater than about 12 lb/ft$^3$, corresponding to a minimum weight fraction of isobutane of about 70% at the lowest suitable operating pressures. Preferably, isobutane partial density in the reaction mixture is in the range of from about 15 to 35 lb/ft$^3$. A more preferred range is that from about 18 to 30 lb/ft$^3$, while the range from about 19 to 25 lb/ft$^3$ is considered most preferred. These noted preferences with respect to upper limits on isobutane partial density ranges correspond to practical considerations, such as are associated with preferred oxidation reaction pressures and the practicalities of safe oxygen compression, rather than to considerations of optimum process performance.

For purposes of the invention, oxygen concentrations in the reaction mixture less than about 5% mol (%m), calculated on the mixture, are preferred. This limitation relates in large part to considerations of process safety and avoidance of fire and explosion hazards. At higher oxygen concentrations greater pressures are needed to avoid formation of a separate explosive oxygen rich phase and maintain the desired supercritical single phase.

The preference for oxygen concentrations less than about 5% also relates to the fact that higher oxygen concentrations tend to decrease the isobutane partial density. The effect of oxygen on the partial density of isobutane at a given pressure results not only from dilution, but also from the effect of oxygen on the intermolecular attractive forces between the isobutane molecules. While the decrease in isobutane partial density can be overcome by increased pressure, thus permitting the invention to be practiced at greater oxygen concentrations (for instance, 10%m), the increased pressure results in increased equipment cost.

Operation of the invention with an oxygen concentration in the mixture of less than about 3.5%m is more preferred, while operation at a concentration of less than about 2.5%m is still more preferred and a concentration of less than about 2.0%m is considered most preferred. It is also found that the magnitude of TBHP production per unit of reaction volume per unit of time decreases to a relatively small degree as oxygen concentration in the mixture is decreased below about 0.5%m. For this reason, oxygen concentrations in the mixture of 0.1%m and higher are preferred, while concentrations above about 0.2%m are more preferred, and concentrations above about 0.4%m are considered most preferred. Still, even quite low oxygen concentrations, e.g., 0.001%m are very suitable and provide a productivity for TBHP that typically is roughly two-thirds of that obtained in the optimal 0.5 to 1%m oxygen range. Isobutane oxidation under supercritical conditions at very low concentration of oxygen is the subject of the commonly-assigned copending application of H. J. Baumgartner entitled Oxidation of Isobutane in the Dense Phase at Low Oxygen Concentration, Ser. No. 308,630, filed on even date herewith. Moreover, while an upper limit is placed upon oxygen concentration in the reaction mixture for purposes of the invention, no limitation with respect to minimum oxygen concentration need be applied to insure an enhanced productivity of TBHP in comparison to conventional processes—at any suitable oxygen concentration the oxidation reaction process of the invention is characterized by a production of TBHP per unit of reaction volume per unit of time that is substantially greater than that achieved under liquid-phase oxidation at the same oxygen concentration.

The same considerations which apply to preferences for the use of oxygen concentrations less than about 1%m, also apply to the use of an oxygen reactant that is substantially pure oxygen. It is possible for purposes of the invention to use an oxygen reactant a mixture of molecular oxygen with substantial amounts of, for instance, other inert gases. However, use of a reactant other than substantially pure oxygen is not recommended, since there is then encountered a build-up of the inert gas in the reaction mixture, accompanied by a disadvantageous lowering of isobutane partial density at a given pressure.

It will be understood by those skilled in the art that since oxygen is a reactant consumed in the course of the process, the concentration of oxygen will be determined by controlling the oxygen feed rate. Similarly it will be understood that the partial density of the isobutane reactant in the mixture at a given temperature will be largely determined by controlling the total pressure of the system.

It is considered of substantial benefit with respect to avoiding process hazards that the invention is preferably operated within a range of oxygen concentrations well below values conventionally preferred for isobutane oxidation, for instance, the 3 to 7 percent by weight (about 5 to 12%m) preferred range disclosed in U.S. Pat. No. 2,845,461.

On the subject of process safety, it also should be noted that the use of a substantially pure oxygen reactant can give rise to certain process hazards if care is not taken in control over reaction parameters. Specifically, it is important to avoid the creation of a reaction mixture having both a liquid and a vapor phase, i.e., a mixture as represented by operation under prior art conditions (for example, as associated with point B on the plot of the drawing). Under processing with a substantially pure oxygen reactant, the vapor phase of such a two-phase mixture would have a sufficiently high oxygen concentration to pose an explosion hazard. Accordingly, if during operation under the invention the isobutane oxidation is continued to a conversion such that the reaction mixture has a critical temperature greater than the reaction temperature, it is necessary in the interest of safety to control reaction mixture pressure (and density) at a high level so that the reaction mixture is maintained as a single dense (liquid) phase, e.g., as shown by point C in the plot of the drawing, and not a two phase mixture. Apart from the maintenance of a process temperature above the critical temperature of the reaction mixture, the process of the invention can be very beneficially continued in such a single, dense liquid phase under the same conditions of temperature, pressure, isobutane partial density, oxygen concentration, and optionally isobutane conversion and TBHP concentration as are specified for operation in the supercritical phase.

Particular advantage may be realized by practice of certain preferred embodiments of the invention in which TBHP concentration in the reaction mixture is no greater than about 15%m calculated on total mols of isobutane and TBHP in the mixture. Such a preference, it can be observed, also necessarily indicates a preference for isobutane conversion of less than about 30%. Embodiments of the invention subject to these conditions are preferred for reasons relating to oxidation reaction selectivity for TBHP. From the standpoint of optimum utilization of isobutane, it is desirable that the oxidation be conducted to afford high selectivity of the desired product. A balance between the competing objects of maximum productivity for TBHP and acceptable selectivity leads to the preference for operation at a conversion of less than about 30% and a TBHP concentration in the reaction mixture of less than about 15%m. A still more preferred practice is that at a TBHP concentration of less than about 10%m and at a conversion of isobutane to less than about 20%, while operation at a TBHP concentration of less than about 8%m to afford a total conversion of isobutane of between about 5 and 15% is most preferred. It is of very substantial advantage that the direct, noncatalytic isobutane oxidation process of the invention can be practiced at an isobutane conversion level of less than 20% to afford both high TBHP productivity and high selectivity. The prior art liquid-phase process of Winkler et al., in which the TBHP oxidation product was utilized to provide a liquid reaction medium during operation above the 134° C. critical temperature of isobutane, cannot be practiced in a like manner. According to preferred aspects of the process of U.S. Pat. No. 2,845,461, a conversion of at least 20% in the reaction mixture is required before isobutane oxidation above 134° C. can be initiated in order that the reaction is conducted in the liquid phase. Thus, in comparison with preferred practice under the instant invention, isobutane oxidation in the liquid state according to the prior art suffers not only from limitations on TBHP production (per volume per time) but also from restrictions on reaction selectivity.

Under operation of the invention, isobutane oxidation is accomplished at a faster conversion rate, for a given selectivity to TBHP, than under prior art liquid-phase oxidation. Thus, reaction times may be correspondingly decreased in comparison to the art. While reaction time is not a critical variable to successful performance of the invention, it may typically be said that a range between about 20 and 100 minutes is more preferred and a range between about 25 and 75 minutes is most preferred. Extended reaction time at the higher temperatures is generally to be avoided as it promotes TBHP decomposition.

The invention is suitably carried out under principles of either batch or continuous process operation. In one particularly desirable batch (or more accurately semibatch) mode, the invention is practiced with controlled gradual addition of oxygen to the supercritical phase reaction medium containing isobutane at a partial density above the minimum specified value until a desired isobutane conversion is reached or, alternatively, until the isobutane partial density decreases below that which is desired. Oxygen addition is maintained at a rate sufficient to provide the desired oxygen concentration in the mixture. Under preferred continuous modes of practice, oxygen and isobutane are both continuously introduced into a reaction medium at a rate and at a pressure to maintain approximately steady-state operations under desired conditions of isobutane partial density, oxygen concentration and, optionally, isobutane conversion.

An example of operation in a continuous mode is that described in the commonly-assigned copending application of E. G. Foster entitled An Improved Process for Oxidation of Isobutane Ser. No. 308,629, filed on even date herewith. According to the invention of that application, isobutane oxidation is accomplished in a continuous manner in multiple reaction stages operated in a series flow configuration. At least the first stage is operated under supercritical temperature and pressure. Each stage is equipped with means for thorough agitation of the reaction mixture therein. Isobutane is fed to the first stage, effluent is withdrawn from each stage except the last and fed to the next stage, oxygen is fed to each stage, and product is withdrawn from the final stage. The use of three or four reaction stages in such a process is typical, with each stage accomplishing an average conversion of about 2 to 4% of the isobutane introduced thereto.

In view of modes of operation which call for a continued addition of reactants to the reaction mixture, and further in view of limitations upon the concentration in the mixture of each reactant, it is most desirable that provision be made for agitation of the mixture to maintain as near as practical a uniform composition throughout. Localized excursions of oxygen concentration above the specified range and/or of isobutane concentration below the specified value may be expected to have adverse effect upon overall reaction productivity for TBHP. Agitation provided by conventional means, such as a propeller mixer or a pumped circulation loop with mixing nozzles, is very suitable.

Isobutane oxidation in accordance with preferred embodiments of the invention yields a product mixture typically (but by no means necessarily) comprising about 4 to 12 percent by weight (%w) TBHP, about 2 to 7%w tertiary butyl alcohol, about 70 to 90%w isobutane, and minor amounts of water and other oxygenated organic compounds. Product mixtures of the process of the invention can be further processed using conventional techniques (for instance, multiple fractionations and carbonate wash) to separate therefrom isobutane suitable for recycle and a TBHP concentrate suitable for commercial purposes, e.g., as a reactant in other chemical synthesis. In one specific treatment which has been found very suitable, the pressure and temperature of the product mixture are reduced to yield a two phase (vapor and liquid) mixture which is then separated by distillation into an overhead isobutane cut suitable for recycle to the oxidation process of the invention, and a bottom cut rich in TBHP (for example, about 35%w) that may be further processed by conventional means to recover a purified TBHP.

Illustrative Embodiments

A number of semi-batch experimental reaction runs in accordance with the process of the invention were conducted in a 0.307 liter Magnadrive autoclave reactor equipped with a cooling coil, a pressure transducer, thermocouples, a hollow stirring shaft fitted with a gas turbine impeller and two marine propellers, and individual tubing lines for isobutane supply, oxygen supply, and product sampling. All autoclave surfaces in contact with the reaction mixture were constructed of type 316 stainless steel. For purposes of passivating the reactor surfaces so that oxidation was conducted in a medium substantially free of metal ions, prior to initial use, all stainless steel surfaces were soaked in 35% nitric acid for an extended time at room temperature, then flushed thoroughly with deionized water, and soaked with an aqueous 2%w sodium pyrophosphate solution for an extended time at room temperature. Between oxidation runs, the autoclave was rinsed with the sodium pyrophosphate solution and drained, leaving a thin coating on the walls.

In the procedure followed for each oxidation reaction run, there was first added to the passivated autoclave reactor about 0.17 cc of 96%w liquid TBHP to act as a reaction initiator. Each reaction was otherwise noncatalytic, conducted in the absence of any other reaction initiators, catalysts, or solvents. The autoclave was cooled with a dry ice bath and gas evacuated therefrom. A preselected quantity of isobutane charge (99.5%m or greater purity) was then introduced into the reactor. Autoclave contents were heated to a preselected temperature with stirring at about 1100 rpm. Initial pressure of isobutane was noted. Oxygen (99.5% or greater purity), supplied from a calibrated high-pressure reservoir, was introduced into the reactor to give a desired initial concentration. Total pressure of the isobutane and oxygen mixture was noted. After a short induction period, oxygen was continually supplied from the calibrated reservoir in an amount sufficient to maintain a constant total pressure in the autoclave as the oxidation reaction progressed. Progress of the reaction was monitored as a function of the rate of oxygen uptake by the reaction mixture, i.e., by the rate of pressure decrease in the calibrated oxygen reservoir. One or more samples were taken from the reactor at various intervals during each run and analyzed to determine isobutane conversion and TBHP selectivity. Samples were of a small volume, so that their removal from the mixture did not significantly change parameters during subsequent continued reaction. Each of the reaction runs was commenced under supercritical conditions of operating temperature and pressure in the mixture. Some of the runs were continued (at the same constant operating temperature and pressure) to levels of isobutane conversion at which the reaction mixture was a single liquid phase mixture then having a critical temperature above the operating temperature. Generally, for such continued reaction, the critical temperature of the mixture rose to a level exceeding the operating temperature at an isobutane conversion of about 5% for an operating temperature of 145° C., at an isobutane conversion of about 10% for an operating temperature of 155° C., and at an isobutane conversion of about 15% for an operating temperature of 165° C.

Table I presents the conditions under which these illustrative experimental embodiments were performed and the results obtained in terms of isobutane conversion, selectivity to TBHP and tertiary-butyl alcohol (TBA), and productivity for TBHP in gram-mol per liter per hour (mol/l/hr).

TABLE I

| Illustrative Embodiment | Isobutane charge (mol) | Initial isobutane partial density (lb/ft$^3$) | Oxygen concentration (% m) | Total pressure (psig) | Temperature (°C.) | Reaction time (min) | Isobutane conversion (%) | Selectivity to TBHP (% w) | Selectivity to TBA (% w) | Productivity for TBHP (mol/l/hr) |
|---|---|---|---|---|---|---|---|---|---|---|
| 1a | 2.00 | 23.6 | 1.2 | 1320 | 165 | 45.3 | 4.4 | 74.5 | 23.2 | 0.27 |
| b | | | | | | 53.3 | 13.2 | 55.7 | 37.2 | 0.59 |
| 2a | 1.838 | 21.7 | 1.88 | 1440 | 165 | 25.0 | 2.5 | 82.9 | 14.6 | 0.29 |
| b | | | | | | 31.9 | 10.2 | 64.2 | 34.2 | 0.69 |
| 3a | 1.848 | 21.8 | 1.94 | 1198 | 155 | 23.3 | 2.8 | 82.0 | 16.9 | 0.34 |
| b | | | | | | 34.1 | 8.5 | 70.0 | 28.2 | 0.60 |
| 4a | 1.19 | 14.0 | 2.26 | 773 | 155 | 37.2 | 3.7 | 71.8 | 27.5 | 0.16 |
| b | | | | | | 62.5 | 14.0 | 51.8 | 47.2 | 0.25 |
| 5a | 1.63 | 19.2 | 2.02 | 828 | 145 | 38.0 | 2.6 | 81.7 | 17.6 | 0.17 |
| b | | | | | | 71.7 | 8.9 | 71.7 | 27.2 | 0.27 |
| 6a | 1.638 | 19.3 | 2.27 | 990 | 155 | 21.4 | 2.6 | 82.7 | 16.2 | 0.31 |
| b | | | | | | 35.7 | 9.7 | 65.1 | 33.4 | 0.53 |
| 7a | 1.629 | 19.2 | 4.69 | 910 | 145 | 73.8 | 3.9 | 87.3 | 12.1 | 0.14 |
| b | | | | | | 100.7 | 8.6 | 76.5 | 22.4 | 0.20 |
| 8a | 1.633 | 19.2 | 1.82 | 1170 | 165 | 14.3 | 2.8 | 80.9 | 17.6 | 0.49 |
| b | | | | | | 22.2 | 10.9 | 66.5 | 32.3 | 0.97 |

TABLE I-continued

| Illustrative Embodiment | Isobutane charge (mol) | Initial isobutane partial density (lb/ft³) | Oxygen concentration (% m) | Total pressure (psig) | Temperature (°C.) | Reaction time (min) | Isobutane conversion (%) | Selectivity to TBHP (% w) | Selectivity to TBA (% w) | Productivity for TBHP (mol/l/hr) |
|---|---|---|---|---|---|---|---|---|---|---|
| c |  |  |  |  |  | 33.5 | 26.1 | 53.7 | 42.5 | 1.25 |
| 9a | 1.886 | 22.2 | 1.72 | 1100 | 145 | 32.2 | 2.4 | 80.5 | 18.7 | 0.21 |
| b |  |  |  |  |  | 58.4 | 7.7 | 78.5 | 20.6 | 0.36 |
| 10 | 2.057 | 24.2 | 1.63 | 1270 | 135 | 64.2 | 2.1 | 89.3 | 9.4 | 0.11 |
| 11 | 1.638 | 19.3 | 4.92 | 1140 | 155 | 52.0 | 10.1 | 74.5 | 23.9 | 0.44 |

The typical influence of several reaction variables upon performance of the process of the invention can be observed by reference to certain of the data presented in Table I. For instance, with regard to the influence of reaction mixture pressure upon productivity for TBHP, it can be seen that at the same temperature (155° C.) and approximately the same low isobutane conversion levels (2.6 to 3.7%), productivity for TBHP increases from a value of 0.16 mol/l/hr at 773 psig total pressure (embodiment 4a), to 0.31 to 990 psig (embodiment 6a), to 0.34 to 1198 psig (embodiment 3a). Similarly, at a temperature of 155° C. and at an isobutane conversion level of 8.5 to 9.7%, reaction productivity for TBHP increases from 0.53 to 990 psig (embodiment 6b) to 0.60 to 1198 psig (embodiment 3b). Since these embodiments were all the result of operation at relatively low isobutane conversion, under conditions such that the reaction mixture contains isobutane in predominant quantity, the results also indicate the influence of isobutane partial density upon the oxidation reaction performance in general, and TBHP productivity in particular. Thus, it can be seen, for instance, that at an isobutane partial density of 14.0 lb/ft³ (embodiment 4a) the productivity for TBHP (0.16 mol/l/hr) is substantially less than that obtained (0.31 mol/l/hr) at an isobutane partial density of 19.3 lb/ft³ (embodiment 6a), other reaction conditions being comparable.

The typical influence of oxygen concentration on oxidation reaction performance can be realized from the results of embodiments 6b, where production of 0.53 mol/l/hr was achieved at a conversion of 9.7% with an oxygen concentration of 2.27%m, and the results of embodiment 11, where a lesser production of 0.44 mol/l/hr was attained at a conversion of 10.1% with an oxygen concentration of 4.92%m. A like effect is illustrated by comparison of embodiments 5a and 5b with embodiments 7a and 7b, respectively.

Comparative Illustration I

It can be determined on the basis of procedures and results of the examples of U.S. Pat. No. 2,845,461 that the liquid-phase isobutane oxidation process therein described is one of relatively low productivity for TBHP. For instance, in Example I of that prior art patent, isobutane oxidation is conducted in the liquid phase of a vapor-liquid mixture to give a 72% conversion of isobutane with a 46%w selectivity to TBHP at an estimated productivity of about 0.070 mol TBHP per liter of reaction mixture volume per hour. In comparison, operation in accordance with the invention to achieve a like selectivity would be characterized a productivity for TBHP that is roughly an order of magnitude higher than that of the prior art example.

Similarly, in Example II of U.S. Pat. No. 2,845,461, isobutane is oxidized with a conversion of 35% and a selectivity to TBHP of 60%w, in a liquid phase reaction process in which is produced about 0.12 mol TBHP per liter of liquid reaction mixture per hour. Again, for like selectivity, this rate of production is about an order of magnitude less than that which can be achieved under operation of the present invention.

Still further, in Example IV of the U.S. Pat. No. 2,845,461, liquid phase oxidation of isobutane is accomplished at a temperature (135° C.) above the critical temperature of isobutane in a reaction mixture comprising substantial quantities of reaction products which serve as solvent for continued reaction. While the reaction selectivity to TBHP is not specifically reported for this prior art example, it can be seen from the results given that, at a conversion of 50%, the productivity for TBHP is less than twice that of Example I of U.S. Pat. No. 2,845,461, and thus remains substantially less than that which can be achieved by operation in accordance with the invention at a like conversion level.

In another mode of comparison, although the rate of conversion of isobutane generally increases substantially with increasing concentration of TBHP in the reaction mixture (at least in the range of concentrations here of interest), it can be seen that the productivity for TBHP achieved in the prior art examples of U.S. Pat. No. 2,845,461 at very high (35 to 72%) conversion is no greater than that achieved at very low (2 to 3%) conversion under practice of the above Illustrative Embodiments.

Comparative Illustration II

Further illustration of the improvement associated with practice according to the invention, in comparison with the prior art, is provided by the results of two successive reaction runs in the same reactor—one in the liquid phase according to teachings of U.S. Pat. No. 2,845,461 and one in the supercritical dense phase according to the present invention. The two reaction runs were accomplished in a one-liter glass-coated autoclave, under the general procedures reported for the Illustrative Embodiments above. In each case the reactor surfaces were considered to have been sufficiently passivated by earlier-performed oxidation reactions. Results are stated in Table II for operation under the prior art practice (run 1) and under the invention (run 2).

TABLE II

| Run number | Isobutane charge (mol) | Oxygen concentration (% m) | Initial isobutane partial density (lb/ft³) | Total pressure (psig) | Temperature (°C.) | Reaction time (min) | Isobutane conversion (%) | Selectivity to TBHP (% w) | Selectivity to TBA (% w) | Productivity for (TBHP (mol/1/hr) |
| --- | --- | --- | --- | --- | --- | --- | --- | --- | --- | --- |
| 1 | 5.53 | 2.3 | 20.0 | 607 | 125 | 492 | 18.0 | 61.8 | 36.0 | 0.069 |
| 2 | 6.09 | 2.1 | 22.0 | 1000 | 155 | 71.7 | 16.1 | 58.5 | 37.5 | 0.44 |

These two reaction runs were each continued to an approximately equivalent level of isobutane conversion. Although selectivity is comparable for the two runs, the mols of TBHP produced per unit volume of reaction mixture per unit of time under liquid-phase reaction condition is substantially less than for practice under the present invention.

Comparative Illustration III

There have been developed certain correlations which provide calculated predictions of isobutane oxidation reaction results, both in the liquid phase according to the prior art and in the supercritical dense phase according to the invention. The validity of these correlations has been tested by comparisons of their predictions with experimental results obtained under given process conditions. The showing of such comparisons in Table III is representative of the typically good agreement between experimental and calculated results. Specifically, this table again illustrates the experimental results of several of the above-described Illustrative Embodiments, together with calculated results for like processing conditions. In the table, reaction rate is indicated in terms of comparative rates of oxygen uptake.

TABLE III

| According to Illustrative Embodiment | Isobutane Conversion (%) | Selectivity to TBHP (% w) Experimental | Selectivity to TBHP (% w) Calculated | Comparative Oxygen Uptake Rates Experimental | Comparative Oxygen Uptake Rates Calculated |
| --- | --- | --- | --- | --- | --- |
| 2a | 2.5 | 82.9 | 82.6 | 10.8 | 16.2 |
| b | 10.2 | 64.2 | 59.8 | 24.0 | 23.0 |
| 3a | 2.8 | 82.0 | 83.3 | 7.8 | 7.6 |
| b | 8.5 | 70.0 | 67.2 | 12.3 | 10.3 |
| 4a | 3.7 | 71.8 | 76.6 | 3.4 | 4.8 |
| b | 14.0 | 51.8 | 50.1 | 5.0 | 5.8 |
| 5a | 2.6 | 81.7 | 85.4 | 2.8 | 2.8 |
| b | 8.9 | 71.7 | 68.4 | 4.5 | 4.0 |
| 6a | 2.6 | 82.7 | 83.4 | 5.0 | 6.4 |
| b | 9.7 | 65.1 | 63.0 | 8.3 | 8.9 |

On the basis of calculations according to these correlations further illustration is provided of the invention and of its results in comparison to the results of the prior art. Table IV presents predictions of process performance in accordance with the invention, for operation of a continuous, single stage reaction, at least initially under supercritical conditions.

TABLE IV

| Temperature (°C.) | Pressure (psig) | Isobutane partial density (lb/ft³) | Oxygen concentration (% m) | Isobutane conversion (%) | Selectivity to TBHP (% mol) | Productivity for TBHP (mol/1/hr) |
| --- | --- | --- | --- | --- | --- | --- |
| 150 | 1000 | 22.0 | 1.0 | 7.7 | 56.2 | 0.52 |
| 150 | 1000 | 22.0 | 1.0 | 15.3 | 42.5 | 0.52 |
| 150 | 1000 | 22.0 | 1.0 | 22.4 | 33.0 | 0.44 |
| 150 | 1200 | 23.5 | 1.0 | 9.4 | 53.4 | 0.60 |
| 150 | 1200 | 23.5 | 1.0 | 17.8 | 39.4 | 0.56 |

Table V presents the results of calculations of process performance not in accordance with the invention. Again the calculations were made on the basis of a continuous, single stage reaction. For purposes of comparison with the invention, certain of the calculations were made for a liquid-phase reaction, (at 130° C.) in accordance with U.S. Pat. No. 2,845,461, while others represent operation at a level of isobutane partial density, i.e., 10.7 lb/ft³, that is below that specified for the present invention.

TABLE V

| Temperature (°C.) | Pressure (psig) | Isobutane partial density (lb/ft³) | Oxygen concentration (% m) | Isobutane conversion (%) | Selectivity to TBHP (% mol) | Productivity for TBHP (mol/1/hr) |
| --- | --- | --- | --- | --- | --- | --- |
| 130 | 700 | 23.7 | 1.0 | 6.2 | 67.0 | 0.125 |
| 130 | 700 | 23.7 | 1.0 | 12.9 | 54.5 | 0.140 |
| 130 | 700 | 23.7 | 1.0 | 19.8 | 44.3 | 0.132 |
| 150 | 600 | 10.7 | 1.0 | 7.0 | 51.0 | 0.142 |
| 150 | 600 | 10.7 | 1.0 | 11.6 | 41.8 | 0.145 |
| 150 | 600 | 10.7 | 1.0 | 16.8 | 34.0 | 0.137 |

We claim as our invention:

1. A process for the preparation of tertiary-butyl hydroperoxide by direct reaction of isobutane and molecular oxygen characterized by enhanced production per unit of reaction volume per unit of time, which comprises reacting isobutane and molecular oxygen reactants in a reaction mixture comprising isobutane reactant in a partial density of at least about 12 lb/ft³ at a temperature above the critical temperature of the mixture and greater than about 140° C. and at a pressure above the critical pressure of the mixture and greater than about 700 psig.

2. The process of claim 1, wherein the concentration of the molecular oxygen reactant in the reaction mixture is less than about 5.0 percent by mol.

3. The process of claim 1, wherein the reaction mixture comprises tertiary-butyl hydroperoxide in a concentration of no more than about 15 percent by mol, calculated on total isobutane and tertiary-butyl hydroperoxide in the mixture.

4. The process of claim 2, wherein the reaction mixture comprises tertiary-butyl hydroperoxide in a concentration of no more than about 15 percent by mol, calculated on total isobutane and tertiary-butyl hydroperoxide in the mixture.

5. The process of claim 2, wherein the isobutane partial density is between about 15 and 35 lb/ft$^3$.

6. The process of claim 5, wherein the oxygen concentration is in the range from about 0.1 to about 3.5 percent by mol.

7. The process of claim 6, wherein the isobutane partial density is between about 18 and 30 lb/ft$^3$.

8. The process of claim 7, wherein the oxygen concentration is between about 0.2 and 3.5 percent by mol.

9. The process of claim 8, wherein the reaction mixture comprises tertiary-butyl hydroperoxide in a concentration of less than about 10 percent by mol.

10. The process of claim 1, 2, 3, 4 or 7, wherein the temperature is in the range from 140° C. to about 170° C.

11. The process of claim 10, wherein the pressure is greater than 700 psig.

12. The process of claim 11, wherein the temperature is in the range from about 145° to 165° C.

13. The process of claim 12, wherein the pressure is greater than about 800 psig.

14. The process of claim 13, wherein the temperature is in the range from about 150° to 160° C.

15. The process of claim 14, wherein the pressure is in the range from about 900 to 1500 psig.

16. A process for the preparation of tertiary-butyl hydroperoxide by direct reaction of isobutane and molecular oxygen characterized by enhanced production per unit of reaction volume per unit of time, which comprises noncatalytically reacting isobutane and molecular oxygen reactants in a dense-phase reaction mixture comprising isobutane reactant in a partial density of at least about 19 lb/ft$^3$, oxygen reactant in a concentration of between about 0.4 and 2.0 percent by mol, and TBHP product in a concentration of less than about 8 percent by mol calculated on total mols of isobutane and tertiary-butyl hydroperoxide at a temperature in the range from about 150° to 160° C., said temperature being above the critical temperature of the reaction mixture, and at a pressure in the range of about 900 to 1500 psig, said pressure being above the critical pressure of the mixture, to afford a conversion of isobutane reactant between about 5 and 15%.

* * * * *